United States Patent
Grosjacques et al.

(10) Patent No.: US 10,918,581 B2
(45) Date of Patent: Feb. 16, 2021

(54) OXIDATION AGENT PREPARATIONS

(71) Applicant: Henkel AG & Co. KGaA, Duesseldorf (DE)

(72) Inventors: Camille Grosjacques, Hamburg (FR); Sylvia Kerl, Hamburg (DE); Susanne Hagenow, Hamburg (DE); Hartmut Manneck, Barnitz (DE); Astrid Kleen-Fehres, Hamburg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 291 days.

(21) Appl. No.: 16/061,492

(22) PCT Filed: Dec. 15, 2016

(86) PCT No.: PCT/EP2016/081173
§ 371 (c)(1),
(2) Date: Jun. 12, 2018

(87) PCT Pub. No.: WO2017/102936
PCT Pub. Date: Jun. 22, 2017

(65) Prior Publication Data
US 2020/0261333 A1    Aug. 20, 2020

(30) Foreign Application Priority Data
Dec. 18, 2015   (DE) .................. 10 2015 225 895

(51) Int. Cl.
| | | |
|---|---|---|
| A61Q 5/00 | (2006.01) | |
| A61K 8/22 | (2006.01) | |
| A61K 8/19 | (2006.01) | |
| A61K 8/24 | (2006.01) | |
| A61K 8/41 | (2006.01) | |
| A61K 8/55 | (2006.01) | |
| A61Q 5/08 | (2006.01) | |
| A61Q 5/10 | (2006.01) | |

(52) U.S. Cl.
CPC .............. *A61K 8/22* (2013.01); *A61K 8/19* (2013.01); *A61K 8/24* (2013.01); *A61K 8/415* (2013.01); *A61K 8/55* (2013.01); *A61Q 5/08* (2013.01); *A61Q 5/10* (2013.01); *A61K 2800/882* (2013.01)

(58) Field of Classification Search
CPC . A61Q 5/10; A61Q 5/08; A61K 8/411; A61K 8/22; A61K 8/415; A61K 2800/88; A61K 2800/4324; A61K 2800/882; A61K 2800/884; A61K 8/55; A61K 8/36; A61K 8/24; A61K 8/19; A61K 31/215
USPC .......................................................... 424/62
See application file for complete search history.

(56) References Cited

U.S. PATENT DOCUMENTS

| | | | |
|---|---|---|---|
| 5,968,486 A * | 10/1999 | Newell ................. | A61K 8/22 424/62 |
| 7,534,272 B2 * | 5/2009 | Cassier ................. | A61K 8/042 8/101 |
| 9,034,056 B2 | 5/2015 | Weser et al. | |
| 2006/0198803 A1 | 9/2006 | Giniger | |
| 2013/0305463 A1 * | 11/2013 | Uellner ................. | A61K 8/442 8/406 |

FOREIGN PATENT DOCUMENTS

| | | |
|---|---|---|
| DE | 102008062239 A1 | 6/2010 |
| DE | 102011082918 A1 | 3/2013 |
| EP | 2471504 A1 | 7/2012 |
| JP | 2006290857 A | 10/2006 |
| WO | 2005067874 A1 | 7/2005 |
| WO | 2014174230 A2 | 10/2014 |
| WO | 2015090882 A1 | 6/2015 |

OTHER PUBLICATIONS

EPO, International Search Report and Written Opinion issued in International Application No. PCT/EP2016/081173, dated Apr. 20, 2017.

* cited by examiner

*Primary Examiner* — Eisa B Elhilo
(74) *Attorney, Agent, or Firm* — Lorenz & Kopf, LLP

(57) ABSTRACT

A first subject of the present disclosure is a special oxidant preparation for oxidative coloring of keratinous fibers, more particularly human hair, included in a cosmetic carrier
(A) hydrogen peroxide and
(B) at least one acid from the group of sulfuric acid, hydrochloric acid, phosphoric acid, lactic acid, citric acid, malic acid, tartaric acid, maleic acid, succinic acid, oxalic acid, ascorbic acid, phytic acid, gluconic acid, nitric acid, malonic acid, acetic acid and-or $C_3$-$C_{22}$ alkane carboxylic acids,
wherein the oxidant preparation has a pH value of from about 0.5 to about 3.0.
Additional subjects of the present disclosure are methods for oxidative color changing of human hair in which this special oxidant preparation is used.

17 Claims, No Drawings

OXIDATION AGENT PREPARATIONS

CROSS-REFERENCE TO RELATED APPLICATION

This application is a U.S. National-Stage entry under 35 U.S.C. § 371 based on International Application No. PCT/EP2016/081173, filed Dec. 15, 2016 which was published under PCT Article 21(2) and which claims priority to German Application No. 10 2015 225 895.5, filed Dec. 18, 2015, which are all hereby incorporated in their entirety by reference.

TECHNICAL FIELD

The present disclosure relates to the cosmetic sector and special oxidant preparations for oxidative color changing of keratinous fibers, particularly human hair. Additional subjects of the present disclosure are methods for oxidative color changing of human hair in which the special oxidant preparation is used.

BACKGROUND

Changing the color of keratinous fibers, more particularly of hair, constitutes an important area of modern cosmetics. Consequently, the hair's appearance can be adapted both to current fashion trends and also to the particular preferences of each and every person. Various possibilities of changing the color of hair are known to a person skilled in the art. The color of hair can be changed temporarily by employing partially-oxidizing dyes. In this process, dyes already formed diffuse from the colorant into the hair fibers. Dyeing with partially-oxidizing dyes causes less hair damage. The disadvantage, however, is that the colors achieved with partially-oxidizing dyes have a low permanency and can be washed out quickly.

If the consumer wants a long-lasting color result or a tint which is lighter than the original hair color, oxidative colorants are normally used. To achieve permanent, intense colors with corresponding fastness properties, so-called oxidative colorants are used. Such colorants usually contain oxidation dye precursors, so-called developer components and coupler components, which form the dyes per se under the influence of oxidants. Oxidative colorants are exemplified by long-lasting color results.

Shortly before application of an oxidative dye, a first preparation (oxidant preparation) containing hydrogen peroxide as an oxidant is normally mixed with a second preparation (dye cream or dye preparation) containing oxidation dye precursors. Then the keratinous fibers are dyed with this ready-to-use oxidative dye.

Level 3 colorations are often used in the hairdressing field. Level 3 colorations are oxidative coloring agents exemplified by especially good durability and especially good gray coverage.

This good durability and good gray coverage can be achieved with a relatively high ammonia content in the colorations, which leads to strong swelling of the hair and consequently a high diffusion rate of the oxidation dye precursors in the hair. With dark tints of Level 3 colorations, the content of oxidation dye precursors is also comparatively high.

However, this ammonia content is also associated with heavy hair damage.

In the home user field, the user who would not want to tolerate this heavy hair damage with every coloration chooses Level 2 products. Level 2 products are also oxidative coloring agents, but they have lower ammonia content or an alternative, less strongly swelling alkalizing agent is used instead of ammonia. In the home user area, Level 3 and Level 2 products are packaged separately and are sold as separate products, so that the user can choose and apply either a Level 3 or a Level 2 product.

In the hairdressing field, the hairdresser offers their customers a much wider pallet of tints. Therefore, a complete Level 3 color series comprises a pallet of a wide variety of color creams, which are mixed with the normal Level 3 oxidant preparation shortly before application. For capacity and storage reasons, the hairdresser will avoid keeping a complete pallet of tints for Level 3 products and for Level 2 products in stock.

Therefore, the present disclosure addresses the problem of providing the hairdresser a flexible and easy-to-use possibility or method that makes it possible for the hairdresser to produce a Level 2 product from a Level 3 coloring product.

BRIEF SUMMARY

Oxidant preparations and methods of oxidative coloring of human hair are provided. In an exemplary embodiment, an oxidant preparation for oxidative color changing of human hair includes a cosmetic carrier. The oxidant preparation also includes hydrogen peroxide and at least one acid. The acid is selected from one or more of sulfuric acid, hydrochloric acid, phosphoric acid, lactic acid, citric acid, malic acid, tartaric acid, maleic acid, succinic acid, oxalic acid, ascorbic acid, phytic acid, gluconic acid, nitric acid, malonic acid, acetic acid and $C_3$-$C_{22}$ alkane carboxylic acids. The oxidant preparation has a pH value of from about 0.5 to about 3.0.

A method for oxidative coloring of human hair is provided in another embodiment. the method includes mixing a first component (K1) with a second component (K2) to produce a mixture (M1). The mixture (M1) is applied to the hair and allowed to take effect for from about 30 seconds to about 45 minutes. Then, the mixture (M1) is rinsed from the hair. The first component (K1) is an oxidant preparation that includes a cosmetic carrier, hydrogen peroxide, and at least one acid. The acid is selected from one or more of sulfuric acid, hydrochloric acid, phosphoric acid, lactic acid, citric acid, malic acid, tartaric acid, maleic acid, succinic acid, oxalic acid, ascorbic acid, phytic acid, gluconic acid, nitric acid, malonic acid, acetic acid and $C_3$-$C_{22}$ alkane carboxylic acids. The oxidant preparation has a pH value of from about 0.5 to about 3.0. The second component (K2) is a dye preparation that includes at least one oxidation dye precursor and/or at least one alkalizing agent.

A method for oxidative coloring of human hair is provided in yet another embodiment. The method includes mixing a first component (Ka) with a second component (Kb) to produce a first mixture (Ma). The first mixture (Ma) is mixed with a third component (Kc) to produce a second mixture (Mb). The second mixture (Mb) is applied to the hair and allowed to take effect for a period of from about 30 seconds to about 45 minutes. Then, the second mixture (Mb) is rinsed from the hair. The first component (Ka) is an oxidation preparation that includes hydrogen peroxide. The second component (Kb) is an oxidant diluent including at least one acid selected from the group of sulfuric acid, hydrochloric acid, phosphoric acid, lactic acid, citric acid, malic acid, tartaric acid, maleic acid, succinic acid, oxalic acid, ascorbic acid, phytic acid, gluconic acid, nitric acid, malonic acid, acetic acid and $C_3$-$C_{22}$-alkanecarboxylic acids. The first mixture (Ma) is an oxidant preparation including a cosmetic carrier, hydrogen peroxide, and at least one acid. The acid is selected from one or more of sulfuric acid, hydrochloric acid, phosphoric acid, lactic acid, citric acid, malic acid, tartaric acid, maleic acid, succinic acid, oxalic acid, ascorbic acid, phytic acid, gluconic acid, nitric acid, malonic acid, acetic acid and $C_3$-$C_{22}$ alkane carboxylic acids. The oxidant preparation has a pH value of from about 0.5 to about 3.0. The third component (Kc) is a dye preparation including at least one oxidation dye precursor and/or at least one alkalizing agent.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

In the context of the work leading to this present disclosure, it has been found that the use of a special oxidant preparation makes it possible for a hairdresser to generate a Level 2 color system for a tint pallet belonging to a Level 3 coloring without causing a color shift on the dyed hair.

By mixing the special oxidant preparation as contemplated herein with the normal dye cream belonging to the Level 3 color system, the hairdresser can, in this manner, produce a ready-to-use dye whose alkalinity was reduced and matched precisely to hair with a higher degree of damage.

In this manner, the hairdresser can give their customers whose hair has long been dyed with a specific Level 3 product the desired color tint with exactly the same resulting tint. Based on the use of special oxidant preparation, however, the content of alkalizing agents in the application mixture can be purposefully reduced and the application mixture can be adapted to the hair of the customer that has sustained heavier damage due to repeated dyeing.

A first subject of the present disclosure is the special oxidant preparation.

A first subject of the present disclosure is an oxidant preparation for oxidative coloring of keratinous fibers, more particularly human hair, contained in a cosmetic carrier, including
(A) hydrogen peroxide and
(B) at least one acid selected from the group of sulfuric acid, hydrochloric acid, phosphoric acid, lactic acid, citric acid, malic acid, tartaric acid, maleic acid, succinic acid, oxalic acid, ascorbic acid, phytic acid, gluconic acid, nitric acid, malonic acid, acetic acid and-or $C_3$-$C_{22}$ alkane carboxylic acids,
wherein the oxidant preparation has a pH value of from about 0.5 to about 3.0.

In particular, a first subject of the present disclosure is an oxidant preparation for oxidative coloring of keratinous fibers, more particularly human hair, contained in a cosmetic carrier, including
(A) hydrogen peroxide and
(B) at least one acid from the group of sulfuric acid, hydrochloric acid, phosphoric acid, lactic acid, citric acid, malic acid, tartaric acid, maleic acid, succinic acid, oxalic acid, ascorbic acid, phytic acid and/or gluconic acid,
wherein the oxidant preparation has a pH value of from about 0.5 to about 3.0.

The oxidant preparation as contemplated herein is specially tailored to use in the hairdressing field. Shortly before use, the hairdresser mixes the oxidant preparation with a second preparation which contains the oxidation dye precursors and/or alkalizing agents. The ready-to-use agent for oxidative color changing of keratinous fibers is obtained by mixing the oxidant preparation and the second preparation.

Keratinous fibers, keratin-containing fibers or keratin fibers are furs, wool, feathers and, in particular, human hair. Although the agents as contemplated herein are most suitable for lightening and coloring keratinous fibers, they can in principle be used for other purposes.

The product is a product for oxidative color changing of keratinous fibers, i.e. a product that is applied on the human head in order to achieve oxidative coloring, lightening, bleaching or tinting of the hair. In this context, tinting is understood to mean coloring in which the resulting color is lighter than the initial hair color.

The oxidant preparation contains the essential components as contemplated herein in a hydrous carrier, preferably in a suitable hydrous or hydrous-alcoholic carrier. Carriers such as creams, emulsions, gels or surfactant-containing, foaming solutions, such as shampoos, foaming aerosols, foam formulations or other preparations suitable for application on the hair, are used for oxidative dyeing.

The oxidant preparation contains hydrogen peroxide as the oxidant (A).

The concentration of the hydrogen peroxide (A) in the oxidant preparation solution is determined on the one hand by legal requirements and, on the other hand, by the desired lightening effect; from about 0.5 to about 20.0 wt. % solutions in water are preferably used. As contemplated herein, preference is given to oxidant preparations exemplified in that they contain hydrogen peroxide (A) in an amount of from about 0.5 to about 12.5 wt. %, preferably from about 1.0 to about 9.0 wt. %, more preferably from about 1.5 to about 6.5 wt. % and particularly from about 2.0 to about 4.5 wt. % relative to their total weight. All specifications in wt. % are relative to the weight of the hydrogen peroxide contained in the oxidant preparation (calculated as about 100% $H_2O_2$) use in relation to the total weight of the oxidant preparation.

In a particularly preferred embodiment, an oxidant preparation as contemplated herein contains hydrogen peroxide (A) in an amount of from about 0.5 to about 12.5 wt. %, preferably from about 1.0 to about 9.0 wt. %, more preferably from about 1.5 to about 6.5 wt. % and particularly from about 2.0 to about 4.5 wt. % relative to its total weight.

Central characteristics of the oxidant preparation that are essential to the present disclosure are (B) their content of specific acids and their low pH value.

As contemplated herein, the oxidant preparation contains at least one acid selected from the group of sulfuric acid, hydrochloric acid, phosphoric acid, lactic acid, citric acid, malic acid, tartaric acid, maleic acid, succinic acid, oxalic acid, ascorbic acid, phytic acid and/or D-gluconic acid.

Sulfuric acid is an inorganic acid with the empirical formula $H_2SO_4$.

Hydrochloric acid is an inorganic acid with the empirical formula HCl.

Phosphoric acid is an inorganic acid with the empirical formula $H_3PO_4$.

Lactic acid (CAS number 50-21-5) is alternatively called 2-hydroxypropanoic acid or 2-hydroxypropionic acid. Lactic acid is present in the form of two enantiomers (D-lactic acid (CAS number 10326-41-7) and L-lactic acid (CAS number 79-33-4), which the present disclosure comprises in both their isolated form and as a mixture.

Alternatively, citric acid (CAS no. 77-92-9) is also called 2-hydroxypropanoic-1,2,3-tricarboxylic acid, 3-carboxy-3-hydroxyglutaric acid or 2-hydroxy-1,2,3-propanetricarboxylic acid.

Alternatively, malic acid is also called 2-hydroxysuccinic acid or 2-hydroxybutanedioic acid. Malic acid is present in the form of two enantiomers, (D-malic acid (CAS number 636-61-3) and L-malic acid (CAS number 97-67-6), which the present disclosure comprises in both their isolated form and as a mixture.

Tartaric acid is also called 2,3-dihydroxysuccinic acid or 2,3-dihydroxybutanedioic acid. Tartaric acid can be present as an L-enantiomer (CAS no. 87-69-4), a D-enantiomer (CAS no. 147-71-7) and in its meso form (CAS no. 147-73-9). The present disclosure comprises each of these forms, in both their isolated form and as a mixture.

Maleic acid is also called cis-butenedioic acid. Maleic acid has the CAS number 110-16-7.

Succinic acid is alternatively called butandioic acid and has the CAS number 110-15-6.

Oxalic acid is also called ethane diacid and has the CAS number 144-62-7.

Ascorbic acid is also called vitamin C or (5R)-5-[(1S)-1,2-dihydroxyethyl]-3,4-dihydroxy-5-hydrofuran-2-on and has the CAS number 50-81-7.

Phytic acid is also called hexa-phospho-inositol and has the CAS number 83-86-3.

Gluconic acid is also called a dextronic acid or (2R,3S,4R,5R) (2R,3S,4R,5R)-2,3,4,5,6-pentahydroxyhexanoic acid and has the CAS number 526-95-4.

Nitric acid is an inorganic acid with the empirical formula $HNO_3$.

Malonic acid is alternatively called 1,3-propane dicarboxylic acid.

Acetic acid is also called ethane acid.

$C_3$-$C_{22}$-alkane carboxylic acids are alkane acids with from 3 to about 22 carbon atoms. Examples of alkane carboxylic acids are pentanoic acid, hexanoic acid, heptanoic acid, octanoic acid, docosanoic acid (lauric acid), tetradecanoic acid (myristic acid), hexadecanoic acid (palmitic acid) and octadecanoic acid (stearic acid).

The aforementioned acids from the group (B) are added in order to adjust the oxidant preparation to the especially low pH values as contemplated herein. In the process, the strong inorganic acids from the group (B) have been found to be particularly well-suited for adjustment of low pH values. Therefore, it is particularly preferred that the oxidant preparation (B) contains at least one acid selected from the group including sulfuric acid, hydrochloric acid and/or phosphoric acid.

In particularly preferred embodiments, the oxidant preparation as contemplated herein contains (B) sulfuric acid, hydrochloric acid and/or phosphoric acid.

The second characteristic of the oxidant preparation that is essential for the present disclosure is its especially low pH value in the range of from about 0.5 to about 3.0.

The pH value can be measured by employing a gas electrode, for example, which is usually in the form of a combination electrode. The pH values according to the present disclosure are pH values that were measured at a temperature of about 22° C.

A particularly effective reduction of the alkalizing agent content in the color cream (and/or dye preparation) of a Level 3 product is possible when the oxidant preparation has a pH value in the range of from about 0.5 to about 2.6, preferably from about 0.5 to about 2.4, more preferably from about 0.5 to about 2.2, even more preferably from about 0.5 to about 2.0, even more preferably from about 0.5 to about 1.8 and particularly from about 0.5 to about 1.6.

Therefore, in a further particularly preferred embodiment, an oxidant preparation has a pH value in the range of from about 0.5 to about 2.6, preferably from about 0.5 to about 2.4, more preferably from about 0.5 to about 2.2, even more preferably from about 0.5 to about 2.0, even more preferably from about 0.5 to about 1.8 and particularly from about 0.5 to about 1.6.

In order to also reliably keep the pH value in the desired low range, one or multiple additional acids differing from the acids from the group (B) are preferably added to the oxidant preparation. In this context, particular preference is given to the addition of one or multiple acids from an additional group (C), which, in addition to their acidifying effect are also capable of stabilizing the hydrogen peroxide. Particularly preferred additional stabilizing acids can be selected from the group (C) including etidronic acid, benzoic acid, pyridine-2,6-dicarboxylic acid, phthalic acid and/or salicylic acid.

In a further particularly preferred embodiment, an oxidant preparation as contemplated herein also contains
(C) one or multiple acids from the group including etidronic acid, benzoic acid, pyridine-2,6-dicarboxylic acid, phthalic acid and/or salicylic acid.

Etidronic acid is also called 1-hydroxy ethane-1,1 diphosphonic acid.—A further particularly preferred embodiment is an oxidant preparation for oxidative coloring of keratinous fibers, particularly human hair, contained in a hydrous cosmetic carrier containing
(A) hydrogen peroxide and
(B) sulfuric acid and
(C) etidronic acid,
wherein the oxidant preparation has a pH value of from about 0.5 to about 3.0.

A further particularly preferred embodiment is an oxidant preparation for oxidative coloring of keratinous fibers, particularly human hair, contained in a hydrous cosmetic carrier containing
(A) hydrogen peroxide and
(B) sulfuric acid and
(C) etidronic acid,
wherein the oxidant preparation has a pH value of from about 0.5 to about 2.2.

A further particularly preferred embodiment is an oxidant preparation for oxidative coloring of keratinous fibers, particularly human hair, contained in a hydrous cosmetic carrier containing
(A) hydrogen peroxide and
(B) sulfuric acid and
(C) etidronic acid,
wherein the oxidant preparation has a pH value of from about 0.5 to about 1.8.

A further particularly preferred embodiment is an oxidant preparation for oxidative coloring of keratinous fibers, particularly human hair, contained in a hydrous cosmetic carrier containing
(A) hydrogen peroxide and
(B) sulfuric acid and
(C) etidronic acid,
wherein the oxidant preparation has a pH value of from about 0.5 to about 1.6.

A further particularly preferred embodiment is an oxidant preparation for oxidative coloring of keratinous fibers, particularly human hair, contained in a hydrous cosmetic carrier containing (A) hydrogen peroxide and
(B) sulfuric acid and
(C) benzoic acid,
wherein the agent has a pH value of from about 0.5 to about 3.0.

A further particularly preferred embodiment is an oxidant preparation for oxidative coloring of keratinous fibers, particularly human hair, contained in a hydrous cosmetic carrier containing
(A) hydrogen peroxide and
(B) sulfuric acid and
(C) benzoic acid,
wherein the agent has a pH value of from about 0.5 to about 2.2.

A further particularly preferred embodiment is an oxidant preparation for oxidative coloring of keratinous fibers, particularly human hair, contained in a hydrous cosmetic carrier containing
(A) hydrogen peroxide and
(B) sulfuric acid and
(C) benzoic acid,
wherein the agent has a pH value of from about 0.5 to about 1.8.

A further particularly preferred embodiment is an oxidant preparation for oxidative coloring of keratinous fibers, particularly human hair, contained in a hydrous cosmetic carrier containing
(A) hydrogen peroxide and
(B) sulfuric acid and
(C) benzoic acid,
wherein the agent has a pH value of from about 0.5 to about 1.6.

A further particularly preferred embodiment is an oxidant preparation for oxidative coloring of keratinous fibers, particularly human hair, contained in a hydrous cosmetic carrier containing
(A) hydrogen peroxide and
(B) sulfuric acid and
(C) pyridine-2,6-dicarboxylic acid.
wherein the agent has a pH value of from about 0.5 to about 3.0.

A further particularly preferred embodiment is an oxidant preparation for oxidative coloring of keratinous fibers, particularly human hair, contained in a hydrous cosmetic carrier containing
(A) hydrogen peroxide and
(B) sulfuric acid and
(C) pyridine-2,6-dicarboxylic acid.
wherein the agent has a pH value of from about 0.5 to about 2.2.

A further particularly preferred embodiment is an oxidant preparation for oxidative coloring of keratinous fibers, particularly human hair, contained in a hydrous cosmetic carrier containing
(A) hydrogen peroxide and
(B) sulfuric acid and
(C) pyridine-2,6-dicarboxylic acid.
wherein the agent has a pH value of from about 0.5 to about 1.8.

A further particularly preferred embodiment is an oxidant preparation for oxidative coloring of keratinous fibers, particularly human hair, contained in a hydrous cosmetic carrier containing
(A) hydrogen peroxide and
(B) sulfuric acid and
(C) pyridine-2,6-dicarboxylic acid.
wherein the agent has a pH value of from about 0.5 to about 1.6.

A further particularly preferred embodiment is an oxidant preparation for oxidative coloring of keratinous fibers, particularly human hair, contained in a hydrous cosmetic carrier containing
(A) hydrogen peroxide and
(B) sulfuric acid and
(C) phthalic acid.
wherein the agent has a pH value of from about 0.5 to about 3.0.

A further particularly preferred embodiment is an oxidant preparation for oxidative coloring of keratinous fibers, particularly human hair, contained in a hydrous cosmetic carrier containing
(A) hydrogen peroxide and
(B) sulfuric acid and
(C) phthalic acid.
wherein the agent has a pH value of from about 0.5 to about 2.2.

A further particularly preferred embodiment is an oxidant preparation for oxidative coloring of keratinous fibers, particularly human hair, contained in a hydrous cosmetic carrier containing
(A) hydrogen peroxide and
(B) sulfuric acid and
(C) phthalic acid.
wherein the agent has a pH value of from about 0.5 to about 1.8.

A further particularly preferred embodiment is an oxidant preparation for oxidative coloring of keratinous fibers, particularly human hair, contained in a hydrous cosmetic carrier containing
(A) hydrogen peroxide and
(B) sulfuric acid and
(C) phthalic acid.
wherein the agent has a pH value of from about 0.5 to about 1.6.

A further particularly preferred embodiment is an oxidant preparation for oxidative coloring of keratinous fibers, particularly human hair, contained in a hydrous cosmetic carrier containing
(A) hydrogen peroxide and
(B) sulfuric acid and
(C) salicylic acid.
wherein the agent has a pH value of from about 0.5 to about 3.0.

A further particularly preferred embodiment is an oxidant preparation for oxidative coloring of keratinous fibers, particularly human hair, contained in a hydrous cosmetic carrier containing
(A) hydrogen peroxide and
(B) sulfuric acid and
(C) salicylic acid.
wherein the agent has a pH value of from about 0.5 to about 2.2.

A further particularly preferred embodiment is an oxidant preparation for oxidative coloring of keratinous fibers, particularly human hair, contained in a hydrous cosmetic carrier containing
(A) hydrogen peroxide and
(B) sulfuric acid and
(C) salicylic acid.
wherein the agent has a pH value of from about 0.5 to about 1.8.

A further particularly preferred embodiment is an oxidant preparation for oxidative coloring of keratinous fibers, particularly human hair, contained in a hydrous cosmetic carrier containing
(A) hydrogen peroxide and
(B) sulfuric acid and
(C) salicylic acid.
wherein the agent has a pH value of from about 0.5 to about 1.6.

A further particularly preferred embodiment is an oxidant preparation for oxidative coloring of keratinous fibers, particularly human hair, contained in a hydrous cosmetic carrier containing
(A) hydrogen peroxide and
(B) hydrochloric acid and
(C) etidronic acid,
wherein the oxidant preparation has a pH value of from about 0.5 to about 3.0.

A further particularly preferred embodiment is an oxidant preparation for oxidative coloring of keratinous fibers, particularly human hair, contained in a hydrous cosmetic carrier containing
(A) hydrogen peroxide and
(B) hydrochloric acid and
(C) etidronic acid,
wherein the oxidant preparation has a pH value of from about 0.5 to about 2.2.

A further particularly preferred embodiment is an oxidant preparation for oxidative coloring of keratinous fibers, particularly human hair, contained in a hydrous cosmetic carrier containing
(A) hydrogen peroxide and
(B) hydrochloric acid and
(C) etidronic acid,
wherein the oxidant preparation has a pH value of from about 0.5 to about 1.8.

A further particularly preferred embodiment is an oxidant preparation for oxidative coloring of keratinous fibers, particularly human hair, contained in a hydrous cosmetic carrier containing
(A) hydrogen peroxide and
(B) hydrochloric acid and
(C) etidronic acid,
wherein the oxidant preparation has a pH value of from about 0.5 to about 1.6.

A further particularly preferred embodiment is an oxidant preparation for oxidative coloring of keratinous fibers, particularly human hair, contained in a hydrous cosmetic carrier containing
(A) hydrogen peroxide and
(B) hydrochloric acid and
(C) benzoic acid,
wherein the agent has a pH value of from about 0.5 to about 3.0.

A further particularly preferred embodiment is an oxidant preparation for oxidative coloring of keratinous fibers, particularly human hair, contained in a hydrous cosmetic carrier containing
(A) hydrogen peroxide and
(B) hydrochloric acid and
(C) benzoic acid,
wherein the agent has a pH value of from about 0.5 to about 2.2.

A further particularly preferred embodiment is an oxidant preparation for oxidative coloring of keratinous fibers, particularly human hair, contained in a hydrous cosmetic carrier containing
(A) hydrogen peroxide and
(B) hydrochloric acid and
(C) benzoic acid,
wherein the agent has a pH value of from about 0.5 to about 1.8.

A further particularly preferred embodiment is an oxidant preparation for oxidative coloring of keratinous fibers, particularly human hair, contained in a hydrous cosmetic carrier containing
(A) hydrogen peroxide and
(B) hydrochloric acid and
(C) benzoic acid,
wherein the agent has a pH value of from about 0.5 to about 1.6.

A further particularly preferred embodiment is an oxidant preparation for oxidative coloring of keratinous fibers, particularly human hair, contained in a hydrous cosmetic carrier containing
(A) hydrogen peroxide and
(B) hydrochloric acid and
(C) pyridine-2,6-dicarboxylic acid.
wherein the agent has a pH value of from about 0.5 to about 3.0.

A further particularly preferred embodiment is an oxidant preparation for oxidative coloring of keratinous fibers, particularly human hair, contained in a hydrous cosmetic carrier containing
(A) hydrogen peroxide and
(B) hydrochloric acid and
(C) pyridine-2,6-dicarboxylic acid.
wherein the agent has a pH value of from about 0.5 to about 2.2.

A further particularly preferred embodiment is an oxidant preparation for oxidative coloring of keratinous fibers, particularly human hair, contained in a hydrous cosmetic carrier containing
(A) hydrogen peroxide and
(B) hydrochloric acid and
(C) pyridine-2,6-dicarboxylic acid.
wherein the agent has a pH value of from about 0.5 to about 1.8.

A further particularly preferred embodiment is an oxidant preparation for oxidative coloring of keratinous fibers, particularly human hair, contained in a hydrous cosmetic carrier containing
(A) hydrogen peroxide and
(B) hydrochloric acid and
(C) pyridine-2,6-dicarboxylic acid.
wherein the agent has a pH value of from about 0.5 to about 1.6.

A further particularly preferred embodiment is an oxidant preparation for oxidative coloring of keratinous fibers, particularly human hair, contained in a hydrous cosmetic carrier containing
(A) hydrogen peroxide and
(B) hydrochloric acid and
(C) phthalic acid.
wherein the agent has a pH value of from about 0.5 to about 3.0.

A further particularly preferred embodiment is an oxidant preparation for oxidative coloring of keratinous fibers, particularly human hair, contained in a hydrous cosmetic carrier containing
(A) hydrogen peroxide and
(B) hydrochloric acid and
(C) phthalic acid.

wherein the agent has a pH value of from about 0.5 to about 2.2.

A further particularly preferred embodiment is an oxidant preparation for oxidative coloring of keratinous fibers, particularly human hair, contained in a hydrous cosmetic carrier containing
(A) hydrogen peroxide and
(B) hydrochloric acid and
(C) phthalic acid.
wherein the agent has a pH value of from about 0.5 to about 1.8.

A further particularly preferred embodiment is an oxidant preparation for oxidative coloring of keratinous fibers, particularly human hair, contained in a hydrous cosmetic carrier containing
(A) hydrogen peroxide and
(B) hydrochloric acid and
(C) phthalic acid.
wherein the agent has a pH value of from about 0.5 to about 1.6.

A further particularly preferred embodiment is an oxidant preparation for oxidative coloring of keratinous fibers, particularly human hair, contained in a hydrous cosmetic carrier containing
(A) hydrogen peroxide and
(B) hydrochloric acid and
(C) salicylic acid.
wherein the agent has a pH value of from about 0.5 to about 3.0.

A further particularly preferred embodiment is an oxidant preparation for oxidative coloring of keratinous fibers, particularly human hair, contained in a hydrous cosmetic carrier containing
(A) hydrogen peroxide and
(B) hydrochloric acid and
(C) salicylic acid.
wherein the agent has a pH value of from about 0.5 to about 2.2.

A further particularly preferred embodiment is an oxidant preparation for oxidative coloring of keratinous fibers, particularly human hair, contained in a hydrous cosmetic carrier containing
(A) hydrogen peroxide and
(B) hydrochloric acid and
(C) salicylic acid.
wherein the agent has a pH value of from about 0.5 to about 1.8.

A further particularly preferred embodiment is an oxidant preparation for oxidative coloring of keratinous fibers, particularly human hair, contained in a hydrous cosmetic carrier containing
(A) hydrogen peroxide and
(B) hydrochloric acid and
(C) salicylic acid.
wherein the agent has a pH value of from about 0.5 to about 1.6.

A further particularly preferred embodiment is an oxidant preparation for oxidative coloring of keratinous fibers, particularly human hair, contained in a hydrous cosmetic carrier containing
(A) hydrogen peroxide and
(B) phosphoric acid and
(C) etidronic acid,
wherein the oxidant preparation has a pH value of from about 0.5 to about 3.0.

A further particularly preferred embodiment is an oxidant preparation for oxidative coloring of keratinous fibers, particularly human hair, contained in a hydrous cosmetic carrier containing
(A) hydrogen peroxide and
(B) phosphoric acid and
(C) etidronic acid,
wherein the oxidant preparation has a pH value of from about 0.5 to about 2.2.

A further particularly preferred embodiment is an oxidant preparation for oxidative coloring of keratinous fibers, particularly human hair, contained in a hydrous cosmetic carrier containing
(A) hydrogen peroxide and
(B) phosphoric acid and
(C) etidronic acid,
wherein the oxidant preparation has a pH value of from about 0.5 to about 1.8.

A further particularly preferred embodiment is an oxidant preparation for oxidative coloring of keratinous fibers, particularly human hair, contained in a hydrous cosmetic carrier containing
(A) hydrogen peroxide and
(B) phosphoric acid and
(C) etidronic acid,
wherein the oxidant preparation has a pH value of from about 0.5 to about 1.6.

A further particularly preferred embodiment is an oxidant preparation for oxidative coloring of keratinous fibers, particularly human hair, contained in a hydrous cosmetic carrier containing
(A) hydrogen peroxide and
(B) phosphoric acid and
(C) benzoic acid,
wherein the agent has a pH value of from about 0.5 to about 3.0.

A further particularly preferred embodiment is an oxidant preparation for oxidative coloring of keratinous fibers, particularly human hair, contained in a hydrous cosmetic carrier containing
(A) hydrogen peroxide and
(B) phosphoric acid and
(C) benzoic acid,
wherein the agent has a pH value of from about 0.5 to about 2.2.

A further particularly preferred embodiment is an oxidant preparation for oxidative coloring of keratinous fibers, particularly human hair, contained in a hydrous cosmetic carrier containing
(A) hydrogen peroxide and
(B) phosphoric acid and
(C) benzoic acid,
wherein the agent has a pH value of from about 0.5 to about 1.8.

A further particularly preferred embodiment is an oxidant preparation for oxidative coloring of keratinous fibers, particularly human hair, contained in a hydrous cosmetic carrier containing
(A) hydrogen peroxide and
(B) phosphoric acid and
(C) benzoic acid,
wherein the agent has a pH value of from about 0.5 to about 1.6.

A further particularly preferred embodiment is an oxidant preparation for oxidative coloring of keratinous fibers, particularly human hair, contained in a hydrous cosmetic carrier containing (A) hydrogen peroxide and
(B) phosphoric acid and
(C) pyridine-2,6-dicarboxylic acid.
wherein the agent has a pH value of from about 0.5 to about 3.0.

A further particularly preferred embodiment is an oxidant preparation for oxidative coloring of keratinous fibers, particularly human hair, contained in a hydrous cosmetic carrier containing
(A) hydrogen peroxide and
(B) phosphoric acid and
(C) pyridine-2,6-dicarboxylic acid.
wherein the agent has a pH value of from about 0.5 to about 2.2.

A further particularly preferred embodiment is an oxidant preparation for oxidative coloring of keratinous fibers, particularly human hair, contained in a hydrous cosmetic carrier containing
(A) hydrogen peroxide and
(B) phosphoric acid and
(C) pyridine-2,6-dicarboxylic acid.
wherein the agent has a pH value of from about 0.5 to about 1.8.

A further particularly preferred embodiment is an oxidant preparation for oxidative coloring of keratinous fibers, particularly human hair, contained in a hydrous cosmetic carrier containing
(A) hydrogen peroxide and
(B) phosphoric acid and
(C) pyridine-2,6-dicarboxylic acid.
wherein the agent has a pH value of from about 0.5 to about 1.6.

A further particularly preferred embodiment is an oxidant preparation for oxidative coloring of keratinous fibers, particularly human hair, contained in a hydrous cosmetic carrier containing
(A) hydrogen peroxide and
(B) phosphoric acid and
(C) phthalic acid.
wherein the agent has a pH value of from about 0.5 to about 3.0.

A further particularly preferred embodiment is an oxidant preparation for oxidative coloring of keratinous fibers, particularly human hair, contained in a hydrous cosmetic carrier containing
(A) hydrogen peroxide and
(B) phosphoric acid and
(C) phthalic acid.
wherein the agent has a pH value of from about 0.5 to about 2.2.

A further particularly preferred embodiment is an oxidant preparation for oxidative coloring of keratinous fibers, particularly human hair, contained in a hydrous cosmetic carrier containing
(A) hydrogen peroxide and
(B) phosphoric acid and
(C) phthalic acid.
wherein the agent has a pH value of from about 0.5 to about 1.8.

A further particularly preferred embodiment is an oxidant preparation for oxidative coloring of keratinous fibers, particularly human hair, contained in a hydrous cosmetic carrier containing
(A) hydrogen peroxide and
(B) phosphoric acid and
(C) phthalic acid.
wherein the agent has a pH value of from about 0.5 to about 1.6.

A further particularly preferred embodiment is an oxidant preparation for oxidative coloring of keratinous fibers, particularly human hair, contained in a hydrous cosmetic carrier containing
(A) hydrogen peroxide and
(B) phosphoric acid and
(C) salicylic acid.
wherein the agent has a pH value of from about 0.5 to about 3.0.

A further particularly preferred embodiment is an oxidant preparation for oxidative coloring of keratinous fibers, particularly human hair, contained in a hydrous cosmetic carrier containing
(A) hydrogen peroxide and
(B) phosphoric acid and
(C) salicylic acid.
wherein the agent has a pH value of from about 0.5 to about 2.2.

A further particularly preferred embodiment is an oxidant preparation for oxidative coloring of keratinous fibers, particularly human hair, contained in a hydrous cosmetic carrier containing
(A) hydrogen peroxide and
(B) phosphoric acid and
(C) salicylic acid.
wherein the agent has a pH value of from about 0.5 to about 1.8.

A further particularly preferred embodiment is an oxidant preparation for oxidative coloring of keratinous fibers, particularly human hair, contained in a hydrous cosmetic carrier containing
(A) hydrogen peroxide and
(B) phosphoric acid and
(C) salicylic acid.
wherein the agent has a pH value of from about 0.5 to about 1.6.

The amounts of the acids from the group (B) which are used in the oxidant preparation as contemplated herein depend on the strength of the respective acid and, if applicable, on additional alkaline-reacting ingredients present in the oxidant preparation. It is preferable that the oxidant preparation contains one or multiple acids from the group (B) in a total amount of from about 0.5 to about 15.0 wt. %, preferably from about 0.5 to about 10.0 wt. %, more preferably from about 0.5 to about 8.0 wt. % and particularly from about 1.0 to about 6.0 wt. %. In this context, all quantity specifications in wt. % relate to the total weight of all acids from the group (B) in relation to the total weight of the oxidant preparation.

In a further particularly preferred embodiment, an oxidant preparation as contemplated herein contains one or multiple acids from the group (B) in a total amount from about 0.5 to about 15.0 wt. %, preferably from about 0.5 to about 10.0 wt. %, more preferably from about 0.5 to about 8.0 wt. % and particularly from about 1.0 to about 6.0 wt. % relative to its total weight.

The amounts of the acids from the group (C) which are used in the oxidant preparation as contemplated herein also depend on the strength of the respective acid and, if applicable, on additional alkaline-reacting ingredients present in the oxidant preparation. It is preferable that the oxidant preparation contains one or multiple acids from the group (C) in a total amount of from about 0.05 to about 10.0 wt. %, preferably from about 0.1 to about 8.0 wt. %, more preferably from about 0.15 to about 6.0 wt. % and particularly from about 0.17 to about 3.0 wt. %. In this context, all quantity specifications in wt. % relate to the total weight of all acids from the group (C) in relation to the total weight of the oxidant preparation.

In a further particularly preferred embodiment, an oxidant preparation as contemplated herein contains one or multiple acids from the group (C) in a total amount from about 0.05 to about 10.0 wt. %, preferably from about 0.1 to about 8.0 wt. %, more preferably from about 0.15 to about 6.0 wt. % and particularly from about 0.17 to about 3.0 wt. % relative to its total weight.

In order to ensure a rapid and good miscibility of the oxidant preparation with the dye preparation, it is particularly preferred that the oxidant preparation is thickened with one or multiple fatty constituents and is present in the form of an emulsion.

In a further particularly preferred embodiment, an oxidant preparation as contemplated herein contains one or multiple fatty constituents in a total amount from about 1.0 to about 10.0 wt. %, preferably from about 1.5 to about 7.5 wt. %, more preferably from about 2.0 to about 7.0 wt. % and particularly from about 2.5 to about 6.5 wt. % relative to its total weight.

To the extent required by the present disclosure, "fatty constituents" are organic compounds with a water solubility at room temperature (about 22° C.) and atmospheric pressure (about 760 mm Hg) of less than about 1 wt. %, preferably less than about 0.1 wt.-%. The definition of fatty constituents explicitly includes only uncharged (i.e. non-ionic) compounds. Fatty constituents have at least one saturated or unsaturated alkyl group with at least 8 C-atoms. The molecular weight of the fatty constituents is a maximum of about 5000 g/mol, preferably a maximum of about 2500 g/mol and even more preferably a maximum of about 1000 g/mol. The fatty constituents are neither polyoxyalkylated nor polyglycerylated compounds.

The preferred fatty constituents in this context are the constituents from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons. The present disclosure explicitly considers only non-ionic substances to be fatty constituents. Charged compounds such as fatty acids and their salts are not considered to be fatty constituents.

The $C_{12}$-$C_{30}$ fatty alcohols can be saturated, mono or poly unsaturated, linear or branched fatty alcohols with from about 12 to about 30 C-atoms.

Examples of preferred linear, saturated $C_{12}$-$C_{30}$ fatty alcohols are dodecan-1-ol (dodecylalcohol, laurylalcohol), tetradecan-1-ol (tetradecyl alcohol, myristyl alcohol), hexadecan-1-ol (hexadecyl alcohol, cetyl alcohol, palmityl alcohol), octadecan-1-ol (octadecyl alcohol, stearyl alcohol), arachyl alcohol (eicosan-1-ol), heneicosyl alcohol (heneicosan-1-ol) and/or behenyl alcohol (docosan-1-ol).

Preferred linear, unsaturated fatty alcohols are (9Z)-octadec-9-en-1-ol (oleyl alcohol), (9E)-octadec-9-en-1-ol (elaidyl alcohol), (9Z,12Z)-cctadeca-9,12-dien-1-ol (linoleyl alcohol), (9Z,12Z,15Z)-octadeca-9,12,15-trien-1-ol (linolenoyl alcohol), gadoleyl alcohol ((9Z)-ei co s-9-en-1-ol), arachidonyl alcohol ((5Z,8Z, 11Z,14Z)-ei cos a-5,8,11,14-tetraen-1-ol), erucyl alcohol ((13Z)-docos-13-en-1-ol) and/ or brassidyl alcohol ((13E)-docosen-1-o1).

The preferred typical branched fatty alcohols are 2-octyl-dodecanol, 2-hexyl-dodecanol and/or 2-butyl-dodecanol.

To the extent required by the present disclosure, a $C_{12}$-$C_{30}$ fatty acid triglyceride is the triester of the trivalent alcohol glycerin with three equivalent fatty acids. Both identically structured and different fatty acids within a triglyceride molecule can be involved in the ester formation.

To the extent required by the present disclosure, fatty acids are saturated or unsaturated, unbranched or branched, unsubstituted or substituted $C_{12}$-$C_{30}$ carboxylic acids. Unsaturated fatty acids can be unsaturated or polyunsaturated. The C—C double bond(s) of an unsaturated fatty acid can have the cis- or trans configuration.

Fatty acid triglycerides are exemplified by their particular suitability, for which at least one of the ester groups, based on glycerin, is formed with a fatty acid, which is selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-Hexadec-9-enoic acid], oleic acid [(9Z)-octadec-9-enoic acid], elaidic acid [(9E)-octadec-9-enoic acid], erucic acid [(13Z)-Docos-13-enoic acid], linoleic acid [(9Z, 12Z)-octadeca-9,12-dienoic acid, linolenic acid [(9Z,12Z,15Z)-octadeca-9,12,15-trienoic acid, eleostearic acid [(9Z,11E,13E)-octadeca-9,11,3-trienoic acid], arachidonic acid [(5Z,8Z,11Z,14Z)-Icosa-5,8,11,14-trienoic acid] and/or nervonic acid [(15Z)-Tetracos-15-enoic acid].

The fatty acid triglycerides can also be from natural sources. The fatty acid triglycerides occurring in soy bean oil, peanut oil, sunflower oil, macadamia nut oil, drumstick tree oil, apricot kernel oil, manila oil and/or possibly hardened castor oil, and the mixtures thereof are particularly suitable for use in the product as contemplated herein.

A $C_{12}$-$C_{30}$ fatty acid monoglyceride is the monoester of the trivalent alcohol glycerin with an equivalent fatty acid. Either the middle hydroxy group of the glycerin or the final hydroxy group of the glycerin can be esterified with the fatty acid.

The $C_{12}$-$C_{30}$ fatty acid triglycerides are exemplified by their particular suitability, for which at least one hydroxy group of the glycerin is esterified, wherein the fatty acids are selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-Hexadec-9-enoic acid], oleic acid [(9Z)-octadec-9-enoic acid], elaidic acid [(9E)-octadec-9-enoic acid], erucic acid [(13Z)-Docos-13-enoic acid], linoleic acid [(9Z, 12Z)-octadeca-9,12-dienoic acid, linoleic acid [(9Z,12Z,15Z)-octadeca-9,12,15-trienoic acid, eleostearic acid [(9Z,11E,13E)-octadeca-9,11,3-trienoic acid], arachidonic acid [(5Z,8Z,11Z,14Z)-Icosa-5,8,11,14-trienoic acid] or nervonic acid [(15Z)-Tetracos-15-enoic acid].

A $C_{12}$-$C_{30}$ fatty acid diglyceride is the diester of the trivalent alcohol glycerin with two equivalent fatty acids. Either the middle and an independent hydroxy group of the glycerin can be esterified with two equivalent fatty acids or both final hydroxy groups of the glycerin are each esterified with one fatty acid. The glycerin can be esterified with two identically structured or two different fatty acids.

Fatty acid diglycerides are exemplified by their particular suitability, for which at least one of the ester groups, based on glycerin, is formed with a fatty acid, which is selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid

[(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z,12Z,15Z)-octadeca-9,12,15-trienoic acid, eleostearic acid [(9Z,11E,13E)-octadeca-9,11,3-trienoic acid], arachidonic acid [(5Z,8Z,11Z,14Z)-Icosa-5,8,11,14-trienoic acid] and/or nervonic acid [(15Z)-tetracos-15-enoic acid].

Hydrocarbons are compounds consisting exclusively of the atoms carbon and hydrogen with from 8 to about 80 C-atoms. In this context, aliphatic hydrocarbons such as mineral oils, liquid paraffin oils (e.g. paraffinium liquidum or paraffinum perliquidum), isoparaffin oils, semi-solid paraffin oils, paraffin waxes, hard paraffin (paraffinum solidum), vaseline and polydecene are preferred.

Suitable paraffin oils are, particularly, liquid paraffin oils (paraffinum liquidum and paraffinum perliquidum). The most preferred hydrocarbon is paraffinum liquidum, also referred to as white oil. Paraffinum liquidum is a mixture of cleaned, saturated, aliphatic hydrocarbons, which includes mainly hydrocarbon chains with a C-chain distribution from about 25 to about 35 C-atoms.

Preferred fatty constituents are selected from the group of $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons. The $C_{12}$-$C_{30}$ fatty alcohols and/or the hydrocarbons are preferred fatty constituents. The $C_{12}$-$C_{30}$ fatty alcohols are particularly preferred fatty constituents.

In a further particularly preferred embodiment, an oxidant preparation as contemplated herein contains one or multiple $C_{12}$-$C_{30}$ fatty alcohols in a total amount from about 1.0 to about 10.0 wt. %, preferably from about 1.5 to about 7.5 wt. %, more preferably from about 2.0 to about 7.0 wt. % and particularly from about 2.5 to about 6.5 wt. % relative to its total weight.

The oxidant components described above can be used by the hairdresser in a method for oxidative color changing of human hair.

A second subject of the present disclosure is, in particular, a method for the oxidative color changing of human hair, comprising the following steps in the specified sequence
A) mixing a first component (K1) with a second component (K2) to produce a mixture (M1),
B) application of the mixture (M1) on the hair,
C) allowing the mixture (M1) to take effect for a period of from about 30 seconds to about 45 minutes,
D) rinsing the mixture (M1) from the hair,
wherein
the first component (K1) is an oxidant preparation, which is disclosed in detail in the description of the first subject of the present disclosure,
the second component (K2) is a dye preparation, which contains at least one oxidation dye precursor, and/or at least one alkalizing agent.

In the method as contemplated herein, the oxidant preparation (the first component (K1)) is mixed with a dye preparation (the second component (K2)) in step A). The color preparation (K2) is, for example, a commonly available Level 3 dye cream which contains at least one oxidation dye precursor and/or at least one alkalizing agent. The second component (K1) preferably contains at least one oxidation dye precursor of the developer type and at least one oxidation dye precursor of the coupler type. The mixture of (K1) and (K2) can take place, for example, by employing stirring or shaking.

After production of the mixture (M1), it is applied on the hair in step B), wherein the mixture (M1) can be applied on the entire region of the hair to be colored or only on specific parts (such as the hairline or the hair lengths/tips).

After application, the mixture (M1) is left on the hair to take effect for a period of about 30 seconds for about 45 minutes in step C). In the process, it is possible to leave the mixture (M1) on all regions of the hair for a specific time period. In a further embodiment, however, it is also possible to choose different exposure periods for specific regions of the hair so that the exposure period in the region of the hairline, for instance, is longer than the exposure period in the region of the damaged tips.

After the exposure period, the mixture (M1) is rinsed out of the hair in step D). The rinsing can take place with water only or with the assistance of a shampoo.

Steps A) to D) are the steps of a single coloring method, i.e. as contemplated herein, all steps are performed during a coloring process that takes place within a specific time period of a maximum of about 6 hours, preferably within a maximum of about 3 hours.

According to the method, the sequence of steps is also defined and takes place in the sequence A), followed by B), followed by C), followed by D).

The components (K1) and (K2) are preferably mixed together in specific quantity ranges in the method as contemplated herein. The first component (K1) and the second component (K2) can be mixed together, for example, in a quantity ratio of from about 3:1 to about 1:3, preferably from about 2:1 to about 2:1.

In a further preferred embodiment, the method for changing color of human hair is exemplified in that
the first component (K1) and the second component (K2) can be mixed together, for example, in a weight ratio of from about 3:1 to about 1:3, preferably from about 2:1 to about 1:2, particularly preferably from about 1.5:1 to about 1:1.5.

Example: If about 150 g of the oxidant preparation (K1) and about 100 g of the dye preparation (K2) are mixed together, the weight ratio is about 1.5:1.

To reduce the pH value of the dye cream (K2) in comparison with a normal Level 3 coloration, said dye cream is mixed with a special oxidant preparation (K1) adjusted to a particularly low pH value.

The dye cream (K2) is a preparation which preferably contains at least one oxidation dye precursor of the developer type and at least one oxidation dye precursor of the coupler type.

Preferred additional oxidation dye precursors of the developer type can be selected from the group formed from 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N$^1$-bis-(2-hydroxyethyl)-N, N-bis-(4-aminophenyl)-1,3-diamino-propane-2-ol, bis-(2-hydroxy-5-aminophenyl)methane, 1,3-bis-(2,5-di aminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethy 1phenol, 4-amino-2-(1,2-dihydroxy ethyl)phenol, 4-amino-2-(diethylaminomethyl)phenol, 2,4, 5,6-tetraaminopyrimidine, 4-hydroxy-2,5,6-triaminopyrimidine, 2-hydroxy-4,5,6-triaminopyrimidine, 2,3-diamino-6, 7-dihydro-1H,5H-pyrazolo[1,2-a]pyrazol-1-one and the physiologically-tolerated salts thereof.

In a further particularly preferred embodiment, the method for oxidative color changing of human hair is exemplified in that the second component (K2) contains at least one oxidation dye precursor from the group including p-toluylendiamine, 2-(2-hydroxyethyl)-p-phenylenediamine, N,N-bis-(2-hydroxyethyl)-p-phenylenedi amine, 2-methoxy methyl-p-phenylenediamine, N-(4-amino-3-methylphenyl)-N-[3-(1H-imidazol-1-yl)propylamine, bis-(2-hydroxy-5-aminophenyl)methane, 4-aminophenol, 4-amino-3-methylphenol, 4,5-diamino-1-(2-hydroxyethyl) pyrazole, 2,4,5,6-tetraaminopyrimidine, 4-hydroxy-2,5,6-triaminopyrimidine, 2-hydroxy-4,5,6-triaminopyrimidine and/or physiologically-tolerated salts thereof.

During the oxidative dyeing process, coupler components do not achieve any significant coloration by themselves. They always require the presence of developer components. As contemplated herein, coupler components permit at least one substitution of a chemical radical of the coupler through the oxidized form of the developer components. At the same time, covalent bonds form between coupler and developer components.

A suitable coupler component as contemplated herein is preferably selected from at least one compound of one of the following classes:
m-aminophenol and/or the derivatives thereof,
m-dihydroxybenzol and/or the derivatives thereof,
m-diaminobenzol and/or the derivatives thereof,
o-diaminobenzol and/or the derivatives thereof,
o-aminophenol derivatives, such as o-aminophenol,
naphthalene derivatives having at least one hydroxy group,
di- and/or trihydroxybenzene and/or the derivatives thereof,
pyridine derivatives,
pyrimidine derivatives,
monohydroxyindole derivatives and/or monoaminoindole-derivatives,
monohydroxyindoline derivatives and/or monoaminoindoline derivatives,
pyrazolone derivatives, such as 1-phenyl-3-methylpyrazol-5-on,
morpholine derivatives, such as 6-hydroxybenzomorpholine or 6-aminobenzomorpholine,
quinoxaline derivatives, such as 6-methyl-1,2,3,4-tetrahydroquinoxaline,
Mixtures of two or multiple compounds from one or multiple of said classes are likewise preferred according to this embodiment.

Preferred oxidation dye precursors of the coupler type can be selected from the group including 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, diaminophenoxy)ethanol, 1,3-bis(2,4-diaminophenoxy)propane, 1-methoxy-2-amino-4-(2-hydroxyethylamino)benzene, (2-amino-4-[(2-hydroxyethyl)amino]-anisole), 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino) ethanol, 2-({3-[(2-hydroxyethyl)amino]-2-methoxy-5-methylphenyl}amino)ethanol, 2-({3-[(2-hydroxyethyl) amino]-4,5-dimethylphenyl}amino)ethanol, 2-{3-morpholin-4-ylphenyl}amino)ethanol, 3-amino-4-(2-methoxyethoxy)-5-methylphenylamine, 1-amino-3-bis(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-on, 1-naphthol, 1,5-dihydroxynaphthaline, 2,7-dihydroxynaphthaline, 1,7-dihydroxynaphthaline, 1,8-dihydroxynaphthaline, 4-hydroxyindole, 6-hydroxyindole, 7-hydroxyindole, 4-hydroxyindoline, 6-hydroxyindoline, 7-hydroxyindoline or mixtures of said compounds or the physiologically compatible salts thereof.

Furthermore, the component (K2) can also contain one or multiple partially-oxidizing dyes.

The pH value of the component (K2) is alkaline. The alkalizing agents for adjustment of the preferred pH values as contemplated herein can be selected from the group formed from ammonia, alkanolamines, basic amino acids, as well as inorganic alkalizing agents, such as (earth) alkali metal hydroxides, (earth) alkali metal metasilicates, (earth) alkali metal phosphates and (earth) alkali metal hydrogen phosphates. Preferred inorganic alkalizing agents are sodium hydroxide, potassium hydroxide, sodium silicate and sodium metasilicate. Organic alkalizing agents usable as contemplated herein are preferably selected from monoethanolamine, 2-amino-2-methylpropanol and triethanolamine. The basic amino acids usable as alkalizing agents as contemplated herein are preferably selected from the group formed from arginine, lysine, ornithine, and histidine, most particularly arginine. However, it emerged during the examinations of the present disclosure that other agents preferred as contemplated herein are exemplified in that they additionally contain an organic alkalizing agent. One embodiment of the first subject matter of the present disclosure is exemplified in that the agent additionally contains at least one alkalizing agent, which is selected from the group formed from ammonia, alkanolamines and basic amino acids, more particularly from ammonia, monoethanolamine and arginine or the tolerated salts thereof.

The pH value can be measured by employing a gas electrode, for example, which is usually in the form of a combination electrode. The pH values according to the present disclosure are pH values that were measured at a temperature of about 22° C.

The second component (K2) is a dye cream, which is common in a normal Level 3 coloration product. To produce colors with high durability and good gray coverage, therefore, the dye creams contain a proportionally high amount of ammonia.

In the method as contemplated herein, this ammonia content is reduced in a defined and reproducible manner by mixing the dye cream (K2) with the oxidant preparation (K1).

In a further preferred embodiment, the method for changing color of human hair is exemplified in that the component (K2) contains from about 1.0 to about 8.0 wt. %, preferably from about 1.5 to about 6.0 wt. % and particularly from about 1.9 to about 4.5 wt. % ammonia (calculated as ($NH_3$)) in relation to the total weight of the component (K2).

Ammonia is normally used as an about 25% hydrous solution. All quantity specifications in wt. % relate to the total amount of ammonia (calculated as $NH_3$) contained in the component (K2) in relation to the total weight of the dye preparation (K2).

Due to the high content of alkalizing agent (particularly ammonia), the dye preparation (i.e. the second component K2)) has an appropriately high pH value in the alkaline range above about 10.0.

In a further preferred embodiment, the method for oxidative color changing of human hair is exemplified in that the component (K2) contains water and that the pH value of the component (K2) has a value of from about 10.0 to about 10.8, preferably from about 10.1 to about 10.6 and particularly from about 10.1 to about 10.5.

By mixing with the particularly acidic oxidant preparation (K1), this pH value in the ready-to-use agent should be reduced to a define value at which an intense coloring result can be achieved, but hair damage can be avoided insofar as possible. It has been found that hair damage can be reduced significantly when the pH value of the ready-to-use dye agent (i.e. the mixture (M1)) is reduced to a pH value less than about 10 and greater than about 9.

In a further preferred embodiment, the method for changing color of human hair is exemplified in that
the pH value of the mixture (M1) has a value of from about 9.0 to about 10.0, preferably from about 9.5 to about 9.9 and particularly preferably from about 9.65 to about 9.85.

In all embodiments described thus far, the hairdresser was provided with the oxidant preparation (corresponding to component (K1) as a finished preparation. In a further embodiment, however, it is also possible that the hairdresser produces the oxidant preparation (K1) by acidifying a conventional oxidant preparation known from the prior art.

The pH value of the conventional oxidant preparations is normally approximately 3.5. For this conventional oxidant preparation, the hairdresser can now add an acidic concentration containing one or multiple of the acids described above from the group (A) (and/or from the groups (A) and (C)) and thus decrease the pH value of the oxidant preparation to the range as contemplated herein of from about 0.5 to about 3.0, particularly from about 0.5 to about 1.8.

This procedure has the particular advantage that the normal oxidant preparation for the Level 3 product and the dye cream can be used to produce a Level 2 coloration from a Level 3 coloration and the hairdresser only has to purchase and store one acid concentration.

Therefore, a further subject of the present disclosure is, in particular, a method for the oxidative color changing of human hair, comprising the following steps in the specified sequence
A) Mixing a first component (Ka) with a second component (Kb) to produce a first mixture (Ma),
B) Mixing the mixture (Ma) with a third component (Kc) to produce a second mixture (Mb),
C) Application of the second mixture (Mb) on the hair,
D) Allowing the mixture (Mb) to take effect for a period of from about 30 seconds to about 45 minutes,
E) Rinsing the mixture (Mb) from the hair,
wherein
the first component (Ka) is an oxidizing preparation that contains hydrogen peroxide.
the second component (Kb) is an oxidant diluent exemplified in that it contains at least one acid from the group of sulfuric acid, hydrochloric acid, phosphoric acid, lactic acid, citric acid, malic acid, tartaric acid, maleic acid, succinic acid, oxalic acid, ascorbic acid, phytic acid and/or D-gluconic acid.
the mixture (MI) is an oxidant preparation, which was disclosed in detail in the description of the first subject of the present disclosure, and
the third component (Kc) is a dye preparation, which contains at least one oxidation dye precursor, and/or at least one alkalizing agent.

In a first step A) of this method as contemplated herein, the oxidant preparation (Ka) (known from the prior art) is mixed with an oxidant diluent (Kb). The mixture of (Ka) and (Kb) can take place, for example, by employing stirring or shaking.

The oxidant preparation (Ka) contains hydrogen peroxide in a hydrous cosmetic carrier and has a pH value of about 3.5.

The oxidant diluent (Kb) is a separately package preparation which contains an acid of the group (A) described above, in addition to water.

Therefore, the oxidant diluent (Kb) contains at least one acid (A) from the group of sulfuric acid, hydrochloric acid, phosphoric acid, lactic acid, citric acid, malic acid, tartaric acid, maleic acid, succinic acid, oxalic acid, ascorbic acid, phytic acid and/or D-gluconic acid.

A first mixture (Ma) is produced by mixing the oxidant preparation (Ka) with the oxidant diluent (Kb). This first mixture (Ma) is the oxidant preparation, which is disclosed in detail in the description of the first subjection of the present disclosure.

When the components (Ka) and (Ka) are mixed together completely, i.e. producing a homogeneous mixture (Ma), said mixture is in turn mixed with the third component (Kc) in a subsequent step B).

The third component (Kc), again, is normally a Level 3 dye cream used by the hairdresser, which contains at least one oxidation dye precursor and/or at least one alkalizing agent. The second component (Kc) preferably contains at least one oxidation dye precursor of the developer type and at least one oxidation dye precursor of the coupler type.

The mixture of (Ma) and (Kc) can, for example, take place by stirring or shaking, resulting in the second mixture (Mb). Then the second mixture (Mb) is applied to the hair.

Steps A) to E) are the steps of a single coloring method, i.e. as contemplated herein, all steps are performed during a coloring process that takes place within a specific time period of a maximum of about 6 hours, preferably within a maximum of about 3 hours.

According to the method, the sequence of steps are also defined and take place in the sequence A), followed by B), followed by C), followed by D), followed by E).

It has been found to be particularly advantageous that the dilution of the oxidant, i.e. production of the first mixture (Ma) from the conventional oxidant preparation (Ka) and the oxidant diluent (Kb) could be carried out without the dye formation being already initiated due to mixture with the oxidant dye precursors. An equivalent and reproducible coloring result could be achieved in this manner.

For this reason, the production of this first mixture (Ma) from (Ka) and (Kb) in step A) is a key and essential step of the method as contemplated herein.

By contrast, if a conventional oxidative dye has been produced by mixing the components (Ka) and (Kc) and then diluted with (Kb), the dye formation process and the acidification take place in parallel. In this method, the intensity of the final hair coloring was therefore essentially influenced by the duration of time required for the intermixing of components (Kb). The coloring results that were achieved with this method were even less reproducible and varied drastically from dyeing process to dyeing process.

The component (Kc) corresponds to the component (K2) of the method described above. Therefore, the statements made for the preferred embodiments of the component (Kc) apply mutatis mutandis for the component (K2).

The components (Ka) and (Kb) are preferably mixed together in specific quantity ranges in the method as contemplated herein. The first component (Ka) and the second component (Kb) can be mixed together, for example, in a quantity ratio of from about 3:1 to about 1:3, preferably from about 2:1 to about 2:1.

The components (Ka) and (Kc) are preferably mixed together in specific quantity ranges in the method as contemplated herein. The first component (Ka) and the third component (Kc) can be mixed together, for example, in a quantity ratio of from about 3:1 to about 1:3, preferably from about 2:1 to about 2:1.

In a further preferred embodiment, the method for dyeing human hair is exemplified in that
A) the first component (Ka) and the second component (Kb) can be mixed together, for example, in a quantity ratio of from about 3:1 to about 1:3, preferably from about 2:1 to about 2:1 and
B) the first mixture (Ma) and the third component (Kc) can be mixed together, for example, in a quantity ratio of from about 3:1 to about 1:3, preferably from about 2:1 to about 1:2.

As already described above, the method as contemplated herein should give the hairdresser the ability to treat damaged regions of the hair with a less-damaging oxidative dye.

In damaged hair, the cuticula, the cuticle of the hair, is damaged to a greater or lesser degree. As a result, there is generally greater color uptake on damaged hair. Therefore, if the hairline and tips are dyed with the same coloring agent, there is always the risk of an uneven coloring result with heavily damaged hair.

Depending on the degree of damage of the respective hair region, the hairdresser can preferably choose whether they apply the mixture (Mb) in step C) of the method or they apply the mixture (Mb) to only specific hair regions.

In a further preferred embodiment, the method for dyeing human hair is exemplified in that
C) the mixture (Mb) is applied to the hairline or in the region of the hair length/tips.

Furthermore, the hairdresser can also choose to vary the exposure time of the mixture (Mb) on specific hair regions depending on the degree of damage.

After application on the hair, the mixture (Mb) is left on the hair to take effect for a period of about 30 seconds to about 45 minutes in step D). In the process, it is possible to leave the mixture (Mb) on all regions of the hair for a specific time period. In a further embodiment, however, it is also possible to choose different exposure periods for specific regions of the hair so that the exposure period in the region of the hairline, for instance, is longer than the exposure period in the region of the damaged tips.

In a further preferred embodiment, the method for dyeing human hair is exemplified in that
D1) the mixture (Mb) is applied on the hair in the region of the hairline or the hair tips for a period of from about 30 seconds to about 45 minutes and
D2) the mixture (Mb) is applied on the hair in the region which was not treated in step
D1) for a period of from about 30 seconds to about 45 minutes, wherein the application durations of steps D1) and D2) differ by at least about 5 minutes, preferably at least about 10 minutes.

If, for example, the hair is heavily damaged in the overall region also directly at the hairline, the hairdresser can
D1) apply the mixture (Mb) on the hair in the region of the hairline for a period of from about 35 to about 45 minutes and
D2) apply the mixture (Mb) on the hair in the region apart from the hairline for a period of only from about 25 to about 30 minutes.

If only the tips are heavily damaged, the hairdresser can
D1) apply the mixture (Mb) on the hair tips for a period of from about 15 to about 25 minutes and
D2) apply the mixture (Mb) on the hair in the region apart from the hair tips for a period of only from about 25 to about 30 minutes.

In the context of the present disclosure, the hairline is understood to mean the region of the hair directly on the scalp (the first 0 to about 5 cm of the hair).

The hair tips are understood to mean the last from about 5 to about 10 cm of the hair depending on the length of the hair.

Moreover, the components (K1), (K2) (Ka), (Kb) and (Kc) described above can also contain additional active ingredients, adjuvants and additives, such as fatty components, surfactants, nonionic polymers such as vinylpyrrolidinone/vinylacrylate-copolymers, polyvinylpyrrolidinone, vinylpyrrolidinone/vinylacetate-copolymers, polyethylenglycols and polysiloxanes; additional silicones such as volatile or non-volatile, straight-chained, branched or cyclical, cross-linked or non-cross-linked polyalkylsiloxanes (such as dimethicones or cyclomethicones), polyarylsiloxanes and/or polyalkylarylsiloxanes, more particularly polysiloxanes with organofunctional groups such as substituted or unsubstituted amines (amodimethicones), carboxyl-, alkoxy- and/or hydroxyl groups (dimethiconecopolyols), linear polysiloxane(A)-polyoxyalkylene(B)-block copolymers, grafted silicon polymers; cationic polymers such as quaternized cellulose ether, polysiloxanes with quaternary groups, dimethyldiallylammoniumchloride-polymers, acrylamide-dimethyldiallyl-ammonium chloride copolymers, with diethylsulfate quaternated dimethylamino-ethylmethacrylate-vinylpyrrolidinone-copolymers, vinylpyrrolidinone-imidazolinium-methochloride-copolymers and quaternated polyvinylalcohol; zwitterionic and amphoteric polymers; anionic polymers such as polyacrylic acids or cross-linked polyacrylic acids; structurants, such as glucose, malic acid and lactic acid, hair-conditioning compounds such as phospholipides, for example lecithin and kephaline; perfume oils, dimethylisosorbid and cyclodextrine; fiber structure-improving agents, more particularly mono-, di- and oligosaccharides, such as glucose, galactose, fructose, fruit sugar and lactose; dyes for coloring the preparations; anti-dandruff active ingredients such as piroctone olamine, zinc omadine and climbazole; amino acids and oligopeptides; protein hydrolysates on an animal and/or plant basis, as well as in the form of their fatty acid condensation products or, where applicable, anionically or cationically modified derivatives; plant oils; light stabilizers and UV blockers; active ingredients such as panthenol, pantothenic acid, pantolacton, allantoin, pyrrolidinoncarbonic acids and the salts thereof, as well as bisabolol; polyphenols, more particularly hydroxy cinnamic acids, 6,7-dihydroxycumarines, hydroxybenzoic acids, catechins, tannins, leukoanthocyanidine, anthocyanidine, flavanons, flavons and flavonols; ceramides or pseudoceramides; vitamins, provitamins and vitamin precursors; plant extracts; fats and waxes such as fatty alcohols, beeswax, montan wax and paraffins; source and penetration substances such as glycerin, propylene glycolmonoethylether, carbonate, hydrogen carbonate, guanidine, urea, as well as primary, secondary and tertiary phosphates; opacifiers such as latex, styrene/PVP and styrene/acrylamide copolymers; pearl shine concentrates such as ethyleneglycolmono- and -distearate as well as PEG-3-distearate; pigments as well as propellants such as propane-butane-mixtures, $N_2O$, dimethylether, $CO_2$ and air.

With respect to other preferred embodiments of the method as contemplated herein, the statements made regarding the oxidant preparations as contemplated herein apply mutatis mutandis.

EXAMPLES

The following formulations have been produced—unless otherwise stated, all values refer to percentage by weight.

1. Oxidant Preparation (Component (K1))

|  | (K1) V | (K1) E |
|---|---|---|
| Sodium benzoate | 0.1 | 0.1 |
| Dipicolinic acid | 0.1 | 0.1 |
| Di-sodium pyrophosphate | 0.1 | 0.1 |
| 1,2-Propanediol | 1.0 | 1.0 |
| Etidronic acid (1-hydroxyethan-1,1-diphosphonic acid) | 0.2 | 0.2 |
| Paraffinum liquidum | 0.3 | 0.3 |
| Steartrimonium chloride | 0.4 | 0.4 |
| Cetearyl alcohol | 3.4 | 3.4 |
| Ceteareth-20 | 1.0 | 1.0 |
| Phosphoric acid | — | 1.0 |
| Hydrogen peroxide | 6.1 | 6.1 |
| Water | ad 100 | ad 100 |
| pH value | pH = 3.5 | pH = 1.42 |

2. Color Preparation (Component (K2))

| | |
|---|---|
| Polyacrylic acid (ammonium salt) 0.5% hydrous solution | 15.0 |
| Decyloleate | 2.1 |
| Sodium cetearyl sulfate | 1.3 |
| Cetearyl alcohol | 14.9 |
| Glyceryl stearate | 5.4 |
| Linoleamidopropyl PG-dimoniumchloride phosphate | 0.05 |
| EDTA | 0.8 |
| Monoethanolamine | 0.4 |
| Ammonia (25% hydrous solution) | 8.0 |
| Ascorbic acid | 0.1 |
| Sodium dithionite | 0.1 |
| L-Serin0 | 0.3 |
| Polyquaternium-2 | 0.1 |
| p-toluenediamine, sulfate | 0.8 |
| Resorcinol | 0.2 |
| m-aminophenol | 0.04 |
| 4-chlororesorcinol | 0.2 |
| 2-amino-4-[(2-hydroxyethyl)amino]-anisole | 0.02 |
| Water | ad 100 |

3. Application

The oxidant preparation (K1) was mixed in a quantity ratio of about 1:1 with the dye preparation (K2).
The following results were obtained

| | (K1) V + (K2)<br>Comparison | (K1) E + (K2)<br>Present disclosure |
|---|---|---|
| pH value | 10.05 | 9.79 |

4. Formulation Examples

| Oxidant preparation (Component (K1)) | |
|---|---|
| Sodium benzoate | 0.05 |
| Dipicolinic acid | 0.13 |
| Di-sodium pyrophosphate | 0.13 |
| 1,2-Propanediol | 1.00 |
| Etidronic acid (1-hydroxyethan-1,1-diphosphonic acid) | 0.20 |
| Paraffinum liquidum | 20.0 |
| Steartrimonium chloride | 0.39 |
| Cetearyl alcohol | 4.70 |
| Ceteareth-20 | 2.80 |
| Glyceryl stearate | 1.35 |
| Hydrogen peroxide | 3.1 |
| Tartaric acid | ad pH 2.1 |
| Water | ad 100 |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An oxidant preparation for oxidative color changing of keratinous fibers, comprising in a cosmetic carrier
    (A) hydrogen peroxide and
    (B) at least one acid selected from the group of hydrochloric acid, etidronic acid, benzoic acid, pyridine-2, 6-dicarboxylic acid, and phthalic acid,
    wherein the oxidant preparation has a pH value of from about 0.5 to about 1.8.

2. The oxidant preparation according to claim 1, wherein the oxidant preparation comprises—relative to its total weight—
    (A) hydrogen peroxide in an amount of from about 0.5 to about 12.5 wt. %.

3. The oxidant preparation according to claim 1 wherein the oxidant preparation comprises at least one acid from the group (B) in a total amount from about 0.5 to about 15.0 wt. %, relative to an oxidant preparation total weight.

4. The oxidant preparation according to claim 1 wherein the oxidant preparation consists of:
    (A) the hydrogen peroxide,
    (B) the acid, wherein the acid is selected from the group consisting of sulfuric acid, hydrochloric acid, etidronic acid, benzoic acid, phyridine-2,6-dicarboxylic acid, phthalic acid, and combinations thereof,
    one or more fatty constituents having at least one saturated or unsaturated alkyl group with at least 8 carbon atoms, wherein the fatty constituent is non-ionic,
    water,
    sodium benzoate,
    propanediol, and
    steartrimonium chloride.

5. A method for oxidative color changing of human hair, comprising the following steps in the specified sequence:
    A) mixing a first component (K1) with a second component (K2) to produce a mixture (M1),
    B) applying the mixture (M1) on the hair,
    C) allowing the mixture (M1) to take effect for a period of from about 30 seconds to about 45 minutes, and D) rinsing the mixture (M1) from the hair,
wherein
the first component (K1) is an oxidant preparation, wherein the oxidant preparation comprises: a cosmetic carrier; (A) hydrogen peroxide; and (B) at least one acid selected from the group of sulfuric acid and hydrochloric acid; and wherein the oxidant preparation has a pH value of from about 0.5 to about 1.8, and
the second component (K2) is a dye preparation, which comprises at least one oxidation dye precursor, and/or at least one alkalizing agent.

6. The method according to claim 5, wherein
the first component (K1) and the second component (K2) are mixed together, in a weight ratio of from about 3:1 to about 1:3.

7. The method according to claim 5 wherein the second component (K2) comprises at least one oxidation dye precursor selected from the group of p-toluenediamine, 2-(2-hydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propylamine, bis-(2-hydroxy-5-aminophenyl)methane, 4-aminophenol, 4-amino-3-methylphenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine and physiologically-tolerated salts thereof.

8. The method according to claim 5 wherein the component (K2) comprises from about 1.0 to about 8.0 wt. % ammonia (calculated as ($NH_3$)) relative to a total weight of the component (K2).

9. The method according to claim 5 wherein
the component (K2) comprises water and that the pH value of the component (K2) has a value of from about 10.0 to about 10.8.

10. The method according to claim 5 wherein
the pH value of the mixture (M1) has a value of from about 9.0 to about 10.0.

11. A method for oxidative color changing of human hair, comprising the following steps in the specified sequence:
A) mixing a first component (Ka) with a second component (Kb) to produce a first mixture (Ma),
B) mixing the first mixture (Ma) with a third component (Kc) to produce a second mixture (Mb),
C) applying the second mixture (Mb) on the hair,
D) allowing the mixture (Mb) to take effect for a period of from about 30 seconds to about 45 minutes, and
E) rinsing the second mixture (Mb) from the hair,
wherein
the steps A) through E) are performed within a maximum of about 6 hours,
the first component (Ka) is an oxidizing preparation that comprises hydrogen peroxide,
the second component (Kb) is an oxidant diluent comprising at least one acid selected from the group of sulfuric acid and hydrochloric acid,
the first mixture (Ma) is an oxidant preparation comprising: a cosmetic carrier; (A) hydrogen peroxide; and (B) at least one acid selected from the group of sulfuric acid and hydrochloric acid; and wherein the oxidant preparation has a pH value of from about 0.5 to about 1.8, and
the third component (Kc) is a dye preparation, comprising at least one oxidation dye precursor, and/or at least one alkalizing agent.

12. The method according to claim 11, wherein
A) the first component (Ka) and the second component (Kb) are mixed together in a quantity ratio of from about 3:1 to about 1:3, and
B) the first mixture (Ma) and the third component (Kc) are mixed together in a quantity ratio of from about 3:1 to about 1:3.

13. The oxidant preparation of claim 1, wherein the oxidant preparation comprises etidronic acid.

14. The oxidant preparation of claim 1, wherein the oxidant preparation comprises benzoic acid.

15. The oxidant preparation of claim 1, wherein the oxidant preparation comprises phridine-2,6-dicarboxylic acid.

16. The oxidant preparation of claim 1 wherein the oxidation preparation has a pH value of from about 0.5 to about 1.6.

17. The oxidant preparation of claim 1, wherein the oxidant preparation comprises phthalic acid.

* * * * *